(12) United States Patent
Cowden et al.

(10) Patent No.: US 6,521,625 B2
(45) Date of Patent: Feb. 18, 2003

(54) PYRAZINONE THROMBIN INHIBITORS

(75) Inventors: Cameron J. Cowden, Hoddesdon (GB); V. Brett Cooper, Hoddesdon (GB); Daniel J. Rush, Morris Township, NJ (US); Patricia Frech, King of Prussia, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/870,560

(22) Filed: May 31, 2001

(65) Prior Publication Data

US 2002/0004507 A1 Jan. 10, 2002

Related U.S. Application Data

(60) Provisional application No. 60/208,665, filed on Jun. 1, 2000.

(51) Int. Cl.[7] ..................... A61K 31/497; C07D 401/14
(52) U.S. Cl. ................................ 514/255.05; 544/405
(58) Field of Search ....................... 544/405; 514/255.05

(56) References Cited

FOREIGN PATENT DOCUMENTS

| EP | 0 195 212 B1 | 11/1993 |
|---|---|---|
| EP | 0 363 284 B1 | 5/1997 |
| WO | WO 99/11267 | 3/1999 |
| WO | WO 00/75134 A1 | 12/2000 |

OTHER PUBLICATIONS

H. Mack et al., "Design Synthesis and Biological Activity of Novel Rigid Amidino–Phenylalanine Derivatives as Inhibitors of Thrombin", J. Enzyme Inhibition, vol. 9, pp. 73–86 (1995).

F. J. Brown et al., "Design Of Orally Active, Non–Peptidic Inhibitors Of Human Leukocyte Elastase", J. Med. Chem., vol. 37, pp. 1259–1261 (1994).

P.D. Edwards et al., "Design, Synthesis and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole", J. Am. Chem. Soc., vol. 114, pp. 1854–1863 (1992).

*Primary Examiner*—Emily Bernhardt
(74) *Attorney, Agent, or Firm*—Richard S. Parr; Melvin Winokur; Valerie J. Camara

(57) ABSTRACT

Compounds of the invention are useful in inhibiting thrombin and associated thrombotic occlusions and are selected from the group consisting of 3-Fluoro-2-pyridylmethyl-3-(2,2-difluoro-2-(2-pyridyl)ethylamino)-6-chloropyrazin-2-one-1-acetamide polymorphic crystalline Anhydrous Form B, 3-Fluoro-2-pyridylmethyl-3-(2,2-difluoro-2-(2-pyridyl)ethylamino)-6-chloropyrazin-2-one-1-acetamide polymorphic crystalline form Type A Monohydrate, and 3-Fluoro-2-pyridylmethyl-3-(2,2-difluoro-2-(2-pyridyl)ethylamino)-6-chloropyrazin-2-one-1-acetamide polymorphic crystalline form Type B monohydrate, or a pharmaceutically acceptable salt thereof.

10 Claims, No Drawings

PYRAZINONE THROMBIN INHIBITORS

CROSS-REFERENCE TO RELATED APPLICATION

This application claims priority to provisional application No. 60/208,665, filed Jun. 1, 2000.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., J. Amer. Chem. Soc., (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., J. Med. Chem., Vol. 37, pages 1259–1261 (1994) describes orally active, non-peptidic inhibitors of human leukocyte elastase which contain trifluoromethylketone and pyridinone moieties.

H. Mack et al., J. Enzyme Inhibition, Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, and compositions comprising a compound of the invention in a pharmaceutically acceptable carrier. The compositions may optionally include anticoagulants, antiplatelet agents, and thrombolytic agents. The compounds of the invention can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

The compounds of the present invention are polymorphic crystalline forms of the compound 3-Fluoro-2-pyridylmethyl-3-(2,2-difluoro-2-(2-pyridyl)ethylamino)-6-chloropyrazin-2-one-1-acetamide, which has the structure

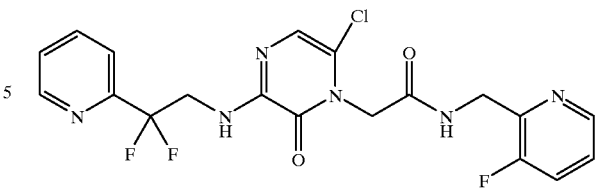

Specifically, the compounds of the invention are selected from the group consisting of 3-Fluoro-2-pyridylmethyl-3-(2,2-difluoro-2-(2-pyridyl)ethylamino)-6-chloropyrazin-2-one-1-acetamide polymorphic crystalline Anhydrous Form B, 3-Fluoro-2-pyridylmethyl-3-(2,2-difluoro-2-(2-pyridyl)ethylamino)-6-chloropyrazin-2-one-1-acetamide polymorphic crystalline form Type A Monohydrate, and 3-Fluoro-2-pyridylmethyl-3-(2,2-difluoro-2-(2-pyridyl)ethylamino)-6-chloropyrazin-2-one-1-acetamide polymorphic crystalline form Type B monohydrate.

Some abbreviations that may appear in this application are as follows:

| ABBREVIATIONS | |
|---|---|
| DCE | 1,2-dichloroethane |
| DMF | dimethylformamide |
| EDC | 1-ethyl-3-(3-dimethylaminopropyl) carbodiimide hydrochloride |
| EtOH | ethanol |
| HCl | hydrochloric acid |
| HOAc | acetic acid |
| HOAT | 1-hydroxy-7-azabenzotriazole |
| iPrOH | 2-propanol |
| KOH | potassium hydroxide |
| MeOH | methanol |
| NCS | N-chlorosuccinimide |
| Pd—C | palladium on activated carbon catalyst |
| PhCH$_3$ | toluene |
| POBr$_3$ | phosphorous oxybromide |
| TEA | triethylamine |

The pharmaceutically-acceptable salts of the compounds of the invention (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors-Therapeutic Uses-Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025 mg/kg/day to 7.5 mg/kg/day, more preferably 0.1 mg/kg/day to 2.5 mg/kg/day, and most preferably 0.1 mg/kg/day to 0.5 mg/kg/day (unless specificed otherwise, amounts of active ingredients are on free base basis). For example, an 80 kg patient would receive between about 0.8 mg/day and 2.4 g/day, preferably 2 mg/day to 600 mg/day, more preferably 8 mg/day to 200 mg/day, and most preferably 8 mg/day to 40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 1.2 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transderrnal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The invention also includes a method for treating an inflammatory disease in a patient which comprises treating the patient with a composition comprising a compound of the present invention. Such diseases include but are not limited to nephritis, systemic lupus erythematosus, rheumatoid arthritis, glomerulonephritis, and sacoidosis.

The invention is also a method for treating an inflammatory disease in a patient that comprises treating the patient with a combination comprising a compound of the invention and an NSAID, e.g., a COX-2 inhibitor. Such diseases include but are not limited to nephritis, systemic lupus, erythematosus, rheumatoid arthritis, glomerulonephritis, vasculitis and sacoidosis.

The present invention is a method for relieving pain, fever and inflammation of a variety of conditions including nephritis, systemic lupus erythematosus, rheumatoid arthritis, glomerulonephritis, sacoidosis, rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures in a patient by administering to the patient a therapeutically effective amount of a compound of the invention. Thrombin inhibitors may also be useful for the treatment of dementia including pre-senile and senile dementia, and in particular, dementia associated with Alzheimer Disease.

In inflammatory diseases wherein fibrin formation is prominent, the fibrin may be a determinant of the pathology. Fibrin serves as a matrix onto which inflammatory cells can migrate and adhere. (see Sherman et al., 1977 *J. Exp. Med.* 145: 76–85; Altieri et al., 1986 *J. Clin. Invest.* 78: 968–976; Wright et al., 1983 *Proc. Natl. Acad. Sci.* 85: 7734–7738; Altieri et al., 1993 *J. Biol. Chem.* 268; 1847–1853). Fibrin also enhances expression of the inflammatory cytokine IL-1beta and decreases expression of IL-1 receptor antagonist by human peripheral blood mononuclear cells (see Perez 1995 *J. immunol.* 154: 1879–1887). The anticoagulants warfarin and heparin attenuate delayed-type hypersensitivity reactions and experimental nephritis in animals. (see Jasain et al., Immunopathogenesis of Rheumatoid Arthritis Eds. G. S. Panayi et al., Surrey, UK, Reedbooks, Ltd. and Halpern et al., 1965 *Nature* 205: 257–259). Enzymatic defibrination with ancrod diminishes the degree of experimental nephritis (Naish et al., 1972 *Clin. Sci.* 42: 643–646), systemic lupus erythematosus (Cole et al., 1990 *Kidney Int.* 37: 29–35, and rheumatoid arthritis (see Busso et al., 1998 *J. Clin. Invest.* 102: 41–50) in animals, and glomerulonephritis in man (see Kim et al., 1988 *Q. J. Med.* 69: 879–905). Additionally, intra articular injection of fibrin induces arthritis in rabbits immunized with fibrin Dumonde et al., 1961 *British Journal of Experimental Pathology* XLIII:373–383), and antigeninduced arthritis in mice is exacerbated in urokinase-deficient mice wherein fibrinolysis synovial fibrin is compromised (see Busso et al., 1998 J. Clin. Invest. 102: 41–50).

In diseases where fibrin deposition is prominent such as, but not limited to, rheumatoid arthritis, systemic lupus erythematosus, glomerulonephritis, vasculitis and sacoidosis, lowering the steady state concentration of fibrin by administration of a compound of the invention will, according to the instant invention, diminish the pathological inflammatory responses associated with these diseases.

Similarly, compounds of the invention will be useful as a partial or complete substitute for conventional NSAIDs in preparations wherein they are presently co-administered with other agents or ingredients. Thus in further aspects, the invention encompasses pharmaceutical compositions for treating inflammatory diseases as defined above comprising a non-toxic therapeutically effective amount of a compound of the invention as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating inflammatory diseases comprising administration to a patient in need of such treatment a non-toxic therapeutically effect amount of a compound of the invention, optionally co-administered with one or more of such ingredients as listed immediately above.

The instant invention also involves a novel combination therapy comprising the administration of a therapeutically effective amount of an NSAID such as a COX-2 inhibitor in combination with a therapeutically effective amount of a compound of the invention to a mammal, and more particularly, to a human. The combination therapy is used to treat inflammatory diseases.

The instant pharmaceutical combinations comprising a compound of the invention in combination with an NSAID such as a COX-2 inhibitor include administration of a single pharmaceutical dosage formulation which contains both a compound of the invention and the NSAID, as well as administration of each active agent in its own separate pharmaceutical dosage formulation. Where separate dosage formulations are used, the compund of the invention and the NSAID can be administered at essentially the same time, i.e., concurrently, or at separately staggered times, i.e, sequentially. The "instant pharmaceutical combination" is understood to include all these regimens. Administration in these various ways are suitable for the present invention as long as the beneficial pharmaceutical effect of the compound of the invention and the NSAID are realized by the patient at substantially the same time. Such beneficial effect is preferably achieved when the target blood level concentrations of each active drug are maintained at substantially the same time. It is preferred that the compound of the invention and the NSAID be co-administered concurrently on a once-a-day dosing schedule; however, varying dosing schedules, such as the compound of the invention once per day and the NSAID once, twice or more times per day, or the NSAID once per day and the compound of the invention once, twice or more times per day, is also encompassed herein. A single oral dosage formulation comprised of both the compound of the invention and the NSAID is preferred. A single dosage formulation will provide convenience for the patient.

The instant invention also provides pharmaceutical compositions comprised of a therapeutically effective amount of an NSAID, or a pharmaceutically acceptable salt thereof, in combination with a therapeutically effective amount of a compound of the invention, or a pharmaceutically acceptable salt thereof, and a pharmaceutically acceptable carrier. One embodiment of the instant compositions is a single composition adapted for oral administration comprised of a therapeutically effective amount of a COX-2 inhibitor in combination with a therapeutically effective amount of a compound of the invention and a pharmaceutically acceptable carrier. The combination can also be administered in separate dosage forms, each having one of the active agents. If administered in separate dosage forms, the separate dosage forms are administered such that the beneficial effect of each active agent is realized by the patient at substantially the same time.

Common NSAIDs include salicylates such as aspirin, sodium salicylate, choline salicylate, salicylsalicylic acid, diflunisal, and salsalate; indoleacetic acids such as indomethacin and sulindac; pyrazoles such as phenylbutazone, oxyphenbutazone; pyrrolealkanoic acids such as tolmetin; phenylacetic acids such as ibuprofen, feroprofen, flurbiprofen, and ketoprofen; fenamates such as mefanamic acid, and meclofenamate; oxicams such as piroxicam; and naphthaleneacetic acids such as naproxen. Cyclo-oxygenase inhibitors such as COX-1 and COX-2 inhibitors are also NSAIDs.

Employing the human whole blood COX-1 assay and the human whole blood COX-2 assay described in C. Brideau et al, Inflamm. Res. 45: 68–74 (1996), herein incorporated by reference, preferably, the compounds have a cyclooxygenase-2 $IC_{50}$ of less than about 2 $\mu$M in the human whole blood COX-2 assay, yet have a cyclooxygenase-1 $IC_{50}$ of greater than about 5 $\mu$M in the human whole blood COX-1 assay. Also preferably, the compounds have a selectivity ratio of cyclooxygenase-2 inhibition over cyclooxygenase-1 inhibition of at least 10, and more preferably of at least 40. The resulting selectivity may indicate an ability to reduce the incidence of common NSAID-induced side effects.

The inhibitor of cyclooxygenase-2 may be administered at a dosage level up to conventional dosage levels for NSAIDs. Suitable dosage levels will depend upon the antiinflammatory effect of the chosen inhibitor of cyclooxygenase-2, but typically suitable levels will be about 0.001 to 50 mg/kg per day, preferably 0.005 to 30 mg/kg per day, and especially 0.05 to 10 mg/kg per day. The compound may be administered on a regimen of up to 6 times per day, preferably 1 to 4 times per day, and especially once per day.

The dosage regimen utilizing a compound of the invention in combination with the NSAID is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts needed to prevent, counter, or arrest the progress of the condition.

Administration of the drug combination to the patient includes both self-administration and administration to the patient by another person.

Additional active agents may be used in combination with the compound of the invention in a single dosage formulation, or may be administered to the patient in a separate dosage formulation, which allows for concurrent or sequential administration. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; vitamin $B_6$ (also known as pyridoxine) and the pharmaceutically acceptable salts thereof such as the HCl salt; vitamin $B_{12}$ (also known as cyanocobalamin); β-adrenergic receptor blockers; folic acid or a pharmaceutically acceptable salt or ester thereof such as the sodium salt and the methylglucamine salt; and antioxidant vitamins such as vitamin C and E and beta carotene.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin and simvastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic Unless otherwise stated, all NMR determinations were made using 400 MHz field strength.

Preparation of 2-Aminomethyl-3-fluoropyridine (A)

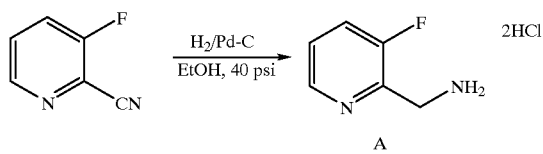

A stirred solution of 6.11 g (50.1 mmol) of 2-cyano-3-fluoropyridine in 250 mL of ethanol and 12.5 mL (150 mmol) of conc. HCl was hydrogenated over 1.90 g of 10% palladium on carbon at 40 psi for 16 h. The catalyst was removed by filtration and the solvents removed at reduced pressure. The resulting solid was diluted with acetonitrile and filtered to give 8.0 g of A as an off-white solid: $^1$H NMR (CD$_3$OD) δ 8.48 (d, 1H, 4.8 Hz), 7.69 (td, 1H, 9.2, 1.1 Hz), 7.68 (ddd, 1H, 8.8, 4.4, 4.4 Hz), 4.34 (s, 2H).

EXAMPLE 1

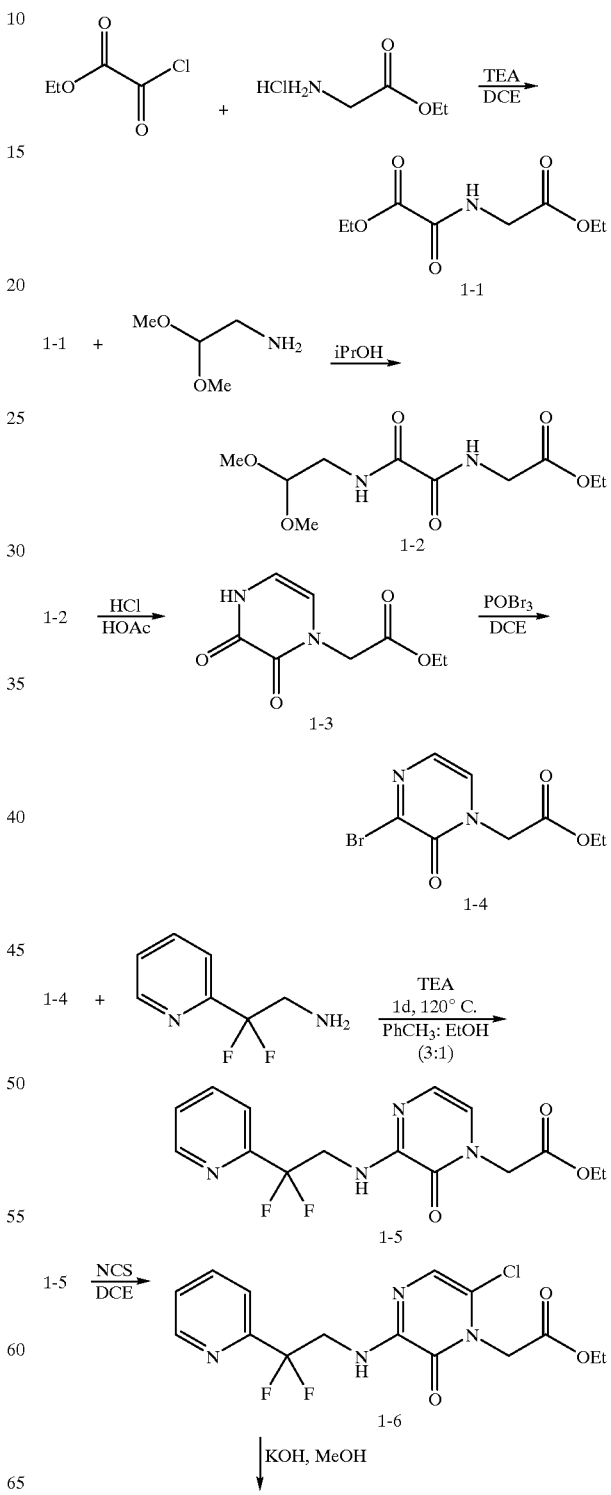

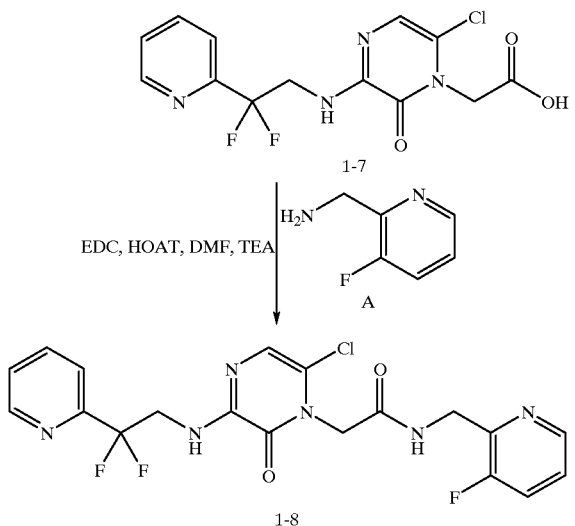

Ethyl N—(ethyl carboxymethyl)oxamate (1—1)

To a suspension of ethyl glycine.HCl (38.4 g, 275 mmol) in 1,2-dichloroethane (360 mL) was added triethylamine (77.0 mL, 550 mmol) at room temperature. After stirring for 30 minutes the heterogenous mixture was cooled to 0° C. and ethyl oxalyl chloride (30.3 mL, 275 mol) was added dropwise over the course of 1 h. Upon completion of the addition, the cooling bath was removed and the reaction was stirred at room temperature overnight. The reaction was diluted with water (250 mL) and the layers separated. The aqueous layer was backwashed with 2 portions of dichloromethane (250 mL). The combined organic layers were washed with water (250 mL), followed by brine (250 mL), dried over MgSO$_4$ and concentrated to give an oil 1—1 that was taken directly onto the next step.

N-(Ethyl carboxymethyl)-N'-(2,2-dimethoxyethyl)oxamide (1—2)

To a solution of the oxamate (84.0 g, 414 mmol) 1—1 in 2-propanol (500 mL) was added aminoacetaldehyde dimethyl acetal (45.7 g, 435 mmol) in one portion. After stirring overnight at room temperature, the reaction mixture was concentrated to a thick orange oil. This thick slurry was diluted with 2-propanol (300 mL) and the solid was broken up with a spatula. Filtration afforded a solid which was further rinsed with an additional portion of 2-propanol. Removal of residual 2-propanol was accomplished via high vacuum to afford a light orange solid 1–2. (89.8 g): $^1$H NMR (CDCl$_3$) δ 7.82 (br s, 1H), 7.50 (br s, 1H), 4.41 (t, 1H, 5.3 Hz), 4.24 (q, 2H, 7.1 Hz), 4.09 (d, 2H, 5.9 Hz), 3.47 (dd, 2H, 5.3, 6.2 Hz), 3.40 (s, 6H), 1.30 (t, 3H, 7.1 Hz).

Ethyl 3-hydroxypyrazin(1H)-2-one-1-acetate (1–3)

A solution of the oxamide (89.8 g, 343 mmol) 1–2, acetic acid (400 mL), and conc. HCl (2 mL) was heated to reflux. After 1 h the black reaction was concentrated to a thick oil (high vacuum employed to ensure complete removal of AcOH) which was diluted with EtOH (150 mL) and MeOH (150 mL). Scraping the thick black oil with a spatula induced precipitation of the product. The MeOH was removed via rotary evaporation and the remaining slurry was filtered and rinsed with EtOH (200 mL) to deliver a tan solid. Recrystallization from refluxing EtOH (300 mL) afforded an off-white powder 1-3: $^1$H NMR (CD$_3$OD) δ 6.50 (d, 1H, 5.9 Hz), 6.36 (d, 1H, 5.9 Hz), 4.58 (s, 2H), 4.23 (q, 2H, 7.1 Hz), 1.28 (t, 3H, 7.1 Hz). Further crude dione could be obtained upon concentration of the mother liquor.

Ethyl 3-bromopyrazin(1H)-2-one-1-acetate (1–4)

A solution of the hydroxypyrazinone (25.0 g, 126 mmol) 1–3 and phosphorous oxybromide (37.9 g, 132 mmol) in 1,2-dichloroethane (250 mL) was heated to reflux. After 8 h the reaction mixture was treated with sat. aq. Na$_2$CO$_3$ (250 mL) and stirred for 1 h. The mixture was diluted with water (100 mL) and dichloromethane (100 mL), the layers were separated and the aqueous layer was backwashed with EtOAc (3×200 mL). The combined organics were dried (MgSO$_4$), and concentrated to give an oil which was stored on a high vacuum line overnite to afford brown solid 1–4: $^1$H NMR (CDCl$_3$) δ 7.17 (d, 1H, 4.2 Hz), 7.07 (d, 1H, 4.2 Hz), 4.65 (s, 2H), 4.27 (q, 2H, 7.2 Hz), 1.31 (t, 3H, 7.2 Hz).

Ethyl 3-(2,2-difluoro-2-(2-pyridylethylamino)pyrazin(1H)-2-one-1-acetate (1–5)

A solution of 4.80 g (30.4 mmol) of 2,2-difluoro-2-(2-pyridyl)ethylamine, 4.24 mL (30.4 mmol) of triethylamine and 7.93 g (30.4 mmol) of ethyl 3-bromopyrazin(1H)-2-one-1-acetate 1–4 was heated to 120° C. in a sealed tube overnight in 12 mL of toluene and 4 mL of ethanol. The reaction was concentrated and the residue was partitioned between dichloromethane and sat. aq. NaHCO$_3$. The aqueous layer was backwashed with 4 portions of dichloromethane. The combined organic layers were dried over MgSO$_4$ and the solvents removed at reduced pressure to give an oil that was chromatographed on SiO$_2$ using 60:40 to 40:60 hexane-EtOAc to give 1–5 as a yellow solid: $^1$H NMR (CDCl$_3$) δ 8.67 (dd, 1H, 4.8, 0.7 Hz), 7.81 (ddd, 1H, 7.8, 7.8, 1.7 Hz), 7.69 (dd, 1H, 7.8, 1 Hz), 7.38 (dd, 1H, 5.1, 7.0 Hz), 6.86 (d, 1H, 4.8 Hz), 6.54 (br t, 1H, 5.9 Hz), 6.40 (d, 1H, 4.6 Hz), 4.54 (s, 2H), 4.38 (td, 2H, 14.0, 6.4 Hz), 4.24 (q, 2H, 7.1 Hz), 1.29 (t, 3H, 7.1 Hz).

Ethyl 3-(2,2-difluoro-2-(2-pyridylethylamino)-6-chloropyrazin(1H)-2-one-1-acetate (1–6)

To a stirred solution of 6.81 g (20.1 mmol) of ethyl 3-(2,2-difluoro-2-(2-pyridylethylamino)pyrazin(1H)-2-one-1-acetate 1–5 and 2.42 g (18.1 mmol) of N-chlorosuccinimide in 100 mL of 1,2-dichloroethane was heated to reflux. An additional 242 mg (1.81 mmol) and 75 mg (0.56 mmol) of NCS were added to the reaction mixture after 1 h and 1.5 h, respectively. After 2.5 h total, the solution was cooled to room temperature and partitioned between dichloromethane (150 mL) and sat. aq. NaHCO$_3$ (200 mL). The layers were separated and the aqueous phase was backwashed with dichloromethane (2×200 mL). The combined organic layers were dried over MgSO$_4$ and the solution concentrated to a volume of 10 mL. This liquid was directly loaded onto a SiO$_2$ column and eluted with 65:35 to 55:45 hexane-EtOAc to give 1–6 as a yellow solid: $^1$H NMR (CDCl$_3$) δ 8.68 (d, 1H, 4.8 Hz), 7.83 (ddd, 1H, 7.7, 7.7, 1.6 Hz), 7.9 (dd, 1H, 7.9 Hz), 7.40 (dd, 1H, 4.9, 7.3 Hz), 6.96 (s, 1H), 6.49 (br t, 1H, 5.9 Hz), 4.89 (s, 2H), 4.38 (td, 2H, 13.9, 6.5 Hz), 4.26 (q, 2H, 7.1 Hz), 1.30 (t, 3H, 7.1 Hz).

3-(2,2-Difluoro-2-(2-pyridylethylamino)-6-chloropyrazin(1H)-2-one-1-acetic acid (1–7)

To a stirred solution of 7.27 g (19.5 mmol) of ethyl 3-(2,2-difluoro-2-(2-pyridylethylamino)-6-chloropyrazin(1H)-2-one-1-acetate 1–6 in 200 mL of methanol was added 39 mL (39.0 mmol) of 1M aq. potassium hydroxide. After 3 h the solution was acidified to pH=7 using conc. HCl, and concentrated at reduced pressure (azeotrope with PhCH$_3$) to give a white solid containing potassium chloride and 1–7: $^1$H NMR (CD$_3$OD) δ 8.64 (d, 1H, 4.8 Hz), 7.93 (ddd, 1H, 7.7, 7.7, 1.5 Hz), 7.70 (d, 1H, 8.0 Hz), 7.49 (dd, 1H, 5.2, 7.4 Hz), 6.80 (s, 1H), 4.67 (s, 2H), 4.27 (t, 2H, 13.9 Hz).

3-Fluoro-2-pyridylmethyl-3-(2,2-difluoro-2-(2-pyridyl)ethylamino)-6-chloropyrazin-2-one-1-acetamide (1–8)

A stirred solution of 330 mg (0.536 mmol) of 3-(2,2-difluoro-2-(2-pyridylethylamino)-6-chloropyrazin(1H)-2-one-1-acetic acid 1–7 and 160 mg (0.805 mmol) 2-aminomethyl-3-fluoropyridine dihydrochloride in 2 mL of DMF was added 128 mg (0.67 mmol) of EDC, 91 mg (0.67 mmol) of HOAT and 0.30 mL (2.1 mmol) triethylamine. After stirring overnite, 80 mg of 2-aminomethyl-3-fluoropyridine dihydrochloride, 128 mg of EDC, 91 mg of HOAT and 0.08 mL (2.1 mmol) triethylamine were added. The reaction was stirred for an additional 24 h and the volatiles were removed en vacuo. The residue was diluted with sat. aq. $NaHCO_3$ (10 mL) and water (15 mL) and filtered to afford a tan solid. This material was chromatographed on $SiO_2$ using 1:99 to 5:95 MeOH—$CH_2Cl_2$ to give a yellow solid 1–8: $^1$H NMR ($CDCl_3$) δ 8.67 (d, 1H, 4.6 Hz), 8.32 (d, 1H, 4.6 Hz), 7.81 (dd, 1H, 7.8, 6.4 Hz), 7.69 (d, 1H, 7.8 Hz), 7.41–7.37 (m, 2H), 7.27–7.22 (m, 2H), 6.97 (s, 1H), 6.49 (br t, 1H, 6.0 Hz), 4.93 (s, 2H), 4.66 (d, 2H, 4.0 Hz), 4.38 (td, 2H, 13.9, 6.5 Hz). 1–8 is also named 2-{3-[(2,2-difluoro-2-(2-pyridyl)ethyl)amino]-6-chloro-2-oxohydropyrazinyl}-N-{(3-fluoro(2-pyridyl))methyl]-acetamide. Conversion to the hydrochloride salt can be carried out by diluting the product with ethyl acetate (2 mL) and treating with 5 mL of 1.5M HCl in ethyl acetate, followed by filtration: $^1$H NMR ($CD_3OD$) δ 8.72 (d, 1H, 4.6 Hz), 8.56 (dd, 1H, 0.9, 5.3 Hz), 8.16–8.11 (m, 2H), 7.87 (d, 1H, 8.1 Hz), 7.80 (ddd, 1H, 4.8, 4.8, 9.0 Hz), 7.68 (dd, 1H, 5.4, 7.2 Hz), 6.87 (s, 1H), 4.95 (s, 2H), 4.74 (d, 2H, 1.1 Hz), 4.35 (t, 2H, 13.8 Hz). Two anhydrous forms and two monohydrate forms of 3-Fluoro-2-pyridylmethyl-3-(2,2-difluoro-2-(2-pyridyl)ethylamino)-6-chloropyrazin-2-one-1-acetamide 1–8 were prepared:

3-Fluoro-2-pyridylmethyl-3-(2,2-difluoro-2-(2-pyridyl)ethylamino)-6-chloropyrazin-2-one-1-acetamide Anhydrous Form A.

A mixture of 3-Fluoro-2-pyridylmethyl-3-(2,2-difluoro-2-(2-pyridyl)ethylamino)-6-chloropyrazin-2-one-1-acetamide 1–8 (0.50 g, 1.10 mmol) and 2-methyl-1-propanol (9 mL) was heated to reflux whereby a solution resulted. After cooling to 22° C. with stirring, filtration of the subsequent mixture afforded the title compound (0.42 g). The Anhydrous Form A has been shown by differential scanning calorimetry, at 5° C./min in an open container under dry nitrogen flow, to have a melting point of approximately 185° C. Thermogravimetric analysis shows it to be essentially anhydrous, with no significant weight loss up to the melting point. The X-ray powder diffraction pattern is characterized by principal d-spacings of 14.21, 10.00, 7.14, 6.35, 5.59, 5.09, 5.01, 4.76, 4.54, 3.35, 3.30 and 2.81 Å.

3-Fluoro-2-pyridylmethyl-3-(2,2-difluoro-2-(2-pyridyl)ethylamino)-6-chloropyrazin-2-one-1-acetamide Anhydrous Form B.

A mixture of 3-Fluoro-2-pyridylmethyl-3-(2,2-difluoro-2-(2-pyridyl)ethylamino)-6-chloropyrazin-2-one-1-acetamide 1–8 (0.50 g, 1.10 mmol) and 2-butanone (9 mL) was heated to reflux and the resulting solution was allowed to cool to 22° C. with stirring. Filtration of the mixture then afforded the title compound (0.36 g). The Anhydrous Form B has been shown by differential scanning calorimetry, at 5° C./min in an open container under dry nitrogen flow, to have a melting point of approximately 179° C. Thermogravimetric analysis shows it to be essentially anhydrous, with no significant weight loss up to the melting point. The X-ray powder diffraction pattern is characterized by principal d-spacings of 16.45, 12.08, 6.81, 5.67, 5.62, 5.05, 4.08, 4.04, 3.96, 3.42, 3.25 and 2.66 Å.

3-Fluoro-2-pyridylmethyl-3-(2,2-difluoro-2-(2-pyridyl)ethylamino)-6-chloropyrazin-2-one-1-acetamide Type A Monohydrate.

A mixture of 3-Fluoro-2-pyridylmethyl-3-(2,2-difluoro-2-(2-pyridyl)ethylamino)-6-chloropyrazin-2-one-1-acetamide 1–8 (2.0 g, 4.42 mmol) and aqueous acetonitrile (40 mL of 1:1) was heated to reflux whereby a solution resulted. This solution was clarified through GF/A filter and then allowed to cool to 22° C. with stirring. Isolation of the resulting solid by filtration afforded the title compound (1.69 g). Type A Monohydrate has been shown by Karl Fischer and thermogravimetric analyses to contain approximately 4% w/w water, consistent with it being a monohydrate. The X-ray powder diffractogram is characterized by principal d-spacings of 14.62, 7.34, 6.70, 6.49, 5.87, 5.61, 5.54, 3.73, 3.67, 3.59, 3.43, 3.23, 3.12 and 2.45 Å.

3-Fluoro-2-pyridylmethyl-3-(2,2-difluoro-2-(2-pyridyl)ethylamino)-6-chloropyrazin-2-one-1-acetamide Type B Monohydrate.

A mixture of 3-Fluoro-2-pyridylmethyl-3-(2,2-difluoro-2-(2-pyridyl)ethylamino)-6-chloropyrazin-2-one-1-acetamide 1–8 (0.50 g, 1.10 mmol), $HCl_{aq}$ (0.55 g of 2M aqueous solution), 2-propanol (10 mL) and water (1 mL) was heated to reflux and the resulting solution was then allowed to cool to 22° C. with stirring. Filtration of the mixture then afforded the title compound (0.38 g). Type B Monohydrate has been shown by Karl Fischer and thermogravimetric analyses to contain approximately 4% w/w water, consistent with it being a monohydrate. The X-ray powder diffractogram is characterized by principal d-spacings of 14.56, 7.30, 6.96, 6.74, 6.05, 5.88, 5.70, 4.65, 4.12, 3.79, 3.66, 3.58, 3.48, 3.43 and 3.01 Å.

Typical tablet cores suitable for administration of thrombin inhibitors are comprised of, but not limited to, the following amounts of standard ingredients:

| Excipient | Suggested % Ranges of Composition for Excipients in Uncoated Tablet Cores | | |
|---|---|---|---|
| | General Range (%) | Preferred Range (%) | Most Preferred Range (%) |
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

Assays of human α-thrombin and human trypsin were performed by the methods substantially as described in Thrombosis Research, Issue No. 70, page 173 (1993) by S. D. Lewis et al. The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

EXAMPLE 2

Tablet Preparation

Tablets containing 8, 10, 20 and 40 mg., respectively, of the following active compounds are prepared as illustrated below (compositions A–C). Active I is one of the following compounds: 3-Fluoro-2-pyridylmethyl-3-(2,2-difluoro-2-(2-pyridyl)ethylamino)-6-chloropyrazin-2-one-1-acetamide polymorphic crystalline Anhydrous Form A, 3-Fluoro-2-pyridylmethyl-3-(2,2-difluoro-2-(2-pyridyl)ethylamino)-6-chloropyrazin-2-one-1-acetamide polymorphic crystalline Anhydrous Form B, 3-Fluoro-2-pyridylmethyl-3-(2,2-difluoro-2-(2-pyridyl)ethylamino)-6-chloropyrazin-2-one-1-acetamide polymorphic crystalline form Type A Monohydrate, or 3-Fluoro-2-pyridylmethyl-3-(2,2-difluoro-2-(2-pyridyl)ethylamino)-6-chloropyrazin-2-one-1-acetamide polymorphic crystalline form Type B monohydrate.

Table for doses containing from 8 to 40 mg of the active compound

| Component | Amount-mg | | | |
|---|---|---|---|---|
| | A | B | C | D |
| Active I | 8 | 10 | 20 | 40 |
| Microcrystalline cellulose | 37.25 | 100 | 200 | 200 |
| Modified food corn starch | 37.25 | 4.25 | 8.5 | 8.5 |
| Magnesium stearate | 0.5 | 0.75 | 1.5 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 3

Tablet Preparation
Exemplary compositions of Active I tablets are shown below:

| Component | 0.25 mg | 2 mg | 10 mg | 50 mg |
|---|---|---|---|---|
| Active I | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

In the table, for example, a tablet containing 2 mg of Active I includes 98.5 mg mannitol, 98.5 mg microcrystalline cellulose, and 1 mg magnesium stearate. 2, 10 and 50 mg tablets were film-coated with an aqueous dispersion of hydroxypropyl cellulose, hydroxypropyl methylcellulose and titanium dioxide, providing a nominal weight gain.

Tablet Preparation Via Direct Compression

Active I, mannitol and microcrystalline cellulose were sieved through mesh screens of specified size (generally 250 to 750 µm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation Via Dry Granulation

Alternatively, a dry powder blend is compacted under modest forces and remilled to afford granules of specified particle size. The granules are then mixed with magnesium stearate and tabletted as stated above.

EXAMPLE 4

Intravenous Formulations

Intravenous formulations of Active I were prepared according to general intravenous formulation procedures.

| Component | Estimated range |
|---|---|
| Active I | 0.12–0.61 mg |
| D-glucuronic acid* | 0.5–5 mg |
| Mannitol NE | 50–53 mg |
| 1 N Sodium Hydroxide | q.s. pH 3.9–4.1 |
| Water for injection | q.s. 1.0 mL |

Exemplary compositions A–C are as follows:

| Component | A | B | C |
|---|---|---|---|
| Active I | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base
**0.25 mg free base
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound selected from the group consisting of 3-Fluoro-2-pyridylmethyl-3-(2,2-difluoro-2-(2-pyridyl)ethylamino)-6-chloropyrazin-2-one-1-acetamide polymorphic crystalline Anhydrous Form B, 3-Fluoro-2-pyridylmethyl-3-(2,2-difluoro-2-(2-pyridyl)ethylamino)-6-chloropyrazin-2-one-1-acetamide polymorphic crystalline form Type A Monohydrate, and 3-Fluoro-2-pyridylmethyl-3-(2,2-difluoro-2-(2-pyridyl)ethylamino)-6-chloropyrazin-2-one-1-acetamide polymorphic crystalline form Type B monohydrate, or a pharmaceutically acceptable salt thereof.

2. The compound of claim 1 which is 3-Fluoro-2-pyridylmethyl -3-(2,2-difluoro-2-(2-pyridyl)ethylamino)-6-chloropyrazin-2-one-1-acetamide polymorphic crystalline Anhydrous Form B, or a pharmaceutically acceptable salt thereof.

3. The compound of claim 1 which is 3-Fluoro-2-pyridylmethyl-3-(2,2-difluoro-2-(2-pyridyl)ethylamino)-6-chloropyrazin-2-one-1-acetamide polymorphic crystalline form Type A Monohydrate, or a pharmaceutically acceptable salt thereof.

4. The compound of claim 1 which is 3-Fluoro-2-pyridylmethyl-3-(2,2-difluoro-2-(2-pyridyl)ethylamino)-6-chloropyrazin-2-one-1-acetamide polymorphic crystalline form Type B Monohydrate, or a pharmaceutically acceptable salt thereof.

5. An oral pharmaceutical composition comprising a compound of claim 1 and a pharmaceutically acceptable carrier.

6. An intravenous pharmaceutical composition comprising a compound of claim 1 and a pharmaceutically acceptable carrier.

7. A method for inhibiting thrombin in blood comprising adding to the blood a composition of claim 5.

8. A process for producing 3-fluoro-2-pyridylmethyl-3-(2,2-difluoro-2-(2-pyridyl)ethylamino)-6-chloropyrazin-2-one-1-acetamide Anhydrous Form B comprising the steps of:
   a) heating a mixture 3-fluoro-2-pyridylmethyl-3-(2,2-difluoro-2-(2-pyridyl)ethylamino)-6-chloropyrazin-2-one-1-acetamide in 2-butanone solvent to form a solution;
   b) cooling the solution and recovering the resultant solid phase; and
   c) removing the solvent therefrom.

9. A process for producing 3-fluoro-2-pyridylmethyl-3-(2,2-difluoro-2-(2-pyridyl)ethylamino)-6-chloropyrazin-2-one-1-acetamide Type A Monohydrate comprising the steps of:
   a) heating a mixture of 3-fluoro-2-pyridylmethyl-3-(2,2-difluoro-2-(2-pyridyl)ethylamino)-6-chloropyrazin-2-one-1-acetamide in aqueous acetonitrile solvent to form a solution;
   b) cooling the solution and recovering the resultant solid phase; and
   c) removing the solvent therefrom.

10. A process for producing 3-fluoro-2-pyridylmethyl-3-(2,2-difluoro-2-(2-pyridyl)ethylamino)-6-chloropyrazin-2-one-1-acetamide Type B Monohydrate comprising the steps of:
   a) heating a mixture 3-fluoro-2-pyridylmethyl-3-(2,2-difluoro-2-(2-pyridyl)ethylamino)-6-chloropyrazin-2-one-1-acetamide in a solvent comprising aqueous hydrochloric acid, 2-propanol, and water to form a solution;
   b) cooling the solution and recovering the resultant solid phase; and
   c) removing the solvent therefrom.

* * * * *